United States Patent [19]
Carver et al.

[11] Patent Number: 6,140,359
[45] Date of Patent: *Oct. 31, 2000

[54] INJECTABLE COMPOSITION

[75] Inventors: David Carver, Boulder; Timothy Prout, Erie; Hernita Ewald, Denver, all of Colo.; Robyn Elliott; Paul Handreck, both of Victoria, Australia

[73] Assignee: NaPro Biotherapeutics, Inc., Boulder, Colo.

[*] Notice: This patent is subject to a terminal disclaimer.

[21] Appl. No.: 09/356,158

[22] Filed: Jul. 19, 1999

Related U.S. Application Data

[62] Division of application No. 08/979,836, Nov. 26, 1997, which is a division of application No. 08/594,478, Jan. 31, 1996, Pat. No. 5,733,888, which is a continuation of application No. 07/995,501, Dec. 22, 1992, abandoned.

[30] Foreign Application Priority Data

Nov. 27, 1992 [AU] Australia ................................. 6074

[51] Int. Cl.⁷ ................................................ A61D 43/02
[52] U.S. Cl. ............................................................. 514/449
[58] Field of Search ............................................. 514/449

[56] References Cited

U.S. PATENT DOCUMENTS

| | | |
|---|---|---|
| 3,864,370 | 2/1975 | Yamashito et al. . |
| 4,814,470 | 3/1989 | Colin et al. ............................. 514/449 |
| 4,942,184 | 7/1990 | Haugwitz et al. ..................... 414/449 |
| 4,960,790 | 10/1990 | Stella et al. ............................ 519/449 |
| 5,157,049 | 10/1992 | Haugwitz et al. ..................... 514/449 |
| 5,254,580 | 10/1993 | Chen et al. ............................. 514/449 |
| 5,281,727 | 1/1994 | Carver et al. . |
| 5,391,385 | 2/1995 | Seybold . |
| 5,403,858 | 4/1995 | Bastard ................................... 514/471 |
| 5,504,102 | 4/1996 | Agharkar et al. ....................... 514/449 |
| 5,733,888 | 3/1998 | Carver et al. ........................... 514/449 |
| 5,972,992 | 10/1999 | Carver et al. ........................... 514/449 |
| 5,977,164 | 11/1999 | Carver et al. ........................... 514/449 |

FOREIGN PATENT DOCUMENTS

| | | |
|---|---|---|
| 32861 | 1/1989 | Australia . |
| 428376 | 5/1991 | European Pat. Off. . |
| 505047 | 9/1992 | European Pat. Off. . |
| 522936 | 1/1993 | European Pat. Off. . |
| 522937 | 1/1993 | European Pat. Off. . |
| 9010443 | 9/1990 | WIPO . |
| 9412198 | 6/1994 | WIPO . |

OTHER PUBLICATIONS

Kingston, David G. I. (1991) The Chemistry of Taxol: Pharmac. Ther. 52:1–34.

Longnecker, et al. (1987) "High Performance Liquid Chromatographic Assay of Taxol in Human Plasma and Pharmacokinetics in Phase I Trial" Cancer Treatment Reports 71(1).

Magri, Neal F. and David G. I. Kingston (1986) "Modified Taxols. 2. Oxidation Products of Taxol" Journal of Org. Chem. 51:797–802.

Mathew, A. E. M. Mejillano, J. P. Nath, R. H. Himes, and V. J. Stella (1992) "Synthesis and Evaluation of Some Water Soluble Prodrugs and Derivatives of taxol and Antitumor Activity," J. Med. Chem. 35:145–51.

Richheimer, Steven L., David M. Tinnermeier and Daniel W. Timmons (1992) "High Performance Liquid Chromatographic Assay of Taxol" Anal. Chem. 64:2323–2326.

Ringel, Israel, Susan Band Horwitz (1987) "Taxol is Converted to 7–Epitaxol, a Biologically Active isomer, in Cell Culture Medium" Journal of Pharmacology and Experimental therapeutics 242(1):692–698.

Waugh, Wanda N., Lawrence A. Trissel and Valentino J. Stella (1991) "Stability, Compatibility, and Plasticizer Extraction of Taxol (NCS–125973) Injection Diluted in infusion Solutions and Stored in Various Containers" Reports Taxol 48 1520–1524.

Rowinsky, E., et al. "Taxol: A Novel Investigational Antimicrotubule Agent" Journal of the National Cancer Institute (1990) 82(15): 1247–59.

Tarr, B.D. et al., "A New Parenteral Vehicle for the Administration of Some Poorly Soluble Anti–Cancer Drugs" J. Parenter. Sci. Technol. (1987) 41(1):31–33.

Trissel, Lawrence (1988) "Monographs on Digoxin, Edrophonium chloride, Etoposide, Hydromorphine Hcl, Methyldopate HC1, Metronidazole, Nalbupine HCl, Phenylephjrine HCl, and Vitamin A" Handbook on Injectible Drugs, 5th Edition.

Dordunoo, Stephen K., and Helen M. Burt (1996) "Solubility and Stability of Taxol: Effects of Buffers and Cyclodextrins" International Journal of Pharmaceutics 133: 191–201.

Kingston, David, G.I. Neal F. Magri, Chote Jitrangsri (1986) "Synthesis and Structure–Activity Relationships of Taxol Derivatives as Anticancer Agents" Studies in Organic Chemistry 26:219–235.

*Primary Examiner*—Keith D. MacMillan
*Attorney, Agent, or Firm*—Saliwanchik, Lloyd & Saliwanchik

[57] ABSTRACT

A pharmaceutical formulation of paclitaxel (also known as taxol) and polyethoxylated castor oil is disclosed to be relatively acidified to a pH of less than 8.1 and preferably within a pH range of 5 to 7, inclusively. Ethanol is optionally included in the formulation which is adapted for use in a body for the treatment of cancer. A formulation method is disclosed and includes the step of mixing an acid with a carrier material, such as polyethoxylated castor oil, to form a carrier solution after which taxol is added in an amount such that the resulting pH is less than 8.1 and preferably in a pH range of 5 to 7. Ethanol may optionally be slurried with the paclitaxel before mixing with the carrier solution. A variety of acidifying agents, a preferred one being anhydrous citric acid, are described.

46 Claims, No Drawings

INJECTABLE COMPOSITION

CROSS-REFERENCE TO A RELATED APPLICATION

This application is a divisional of U.S. Ser. No. 08/979,836, filed Nov. 26, 1997; which is a divisional of U.S. Ser. No. 08/594,478, filed Jan. 31, 1996, now U.S. Pat. No. 5,733,888; which is a continuation of U.S. Ser. No. 07/995,501, filed Dec. 22, 1992, now abandoned.

This invention relates to a solution of taxol having improved stability.

BACKGROUND OF THE INVENTION

Taxol is a compound extracted from the bark of a western yew, *Taxus brevifolia* and known for its antineoplastic activity. It is described for example in The Merck Index, Eleventh Edition 1989, monograph 9049.

In 1977, taxol (paclitaxel) was chosen for development as an antineoplastic agent because of its unique mechanism of action and good cytotoxic activity against IP implanted D16 melanoma and the human X-1 mammary tumor xenograft. Paclitaxel is believed to function as a mitotic spindle poison and as a potent inhibitor of cell replication in vitro. Other mitotic spindle points (colchicine and podophyllotoxin) inhibit microtubule assembly. Paclitaxel employs a different mechanism of action since it appears to shift the equilibrium of polymerimization/depolymerization toward polymer assembly and to stabilize microtubules against depolymerization under conditions which would cause rapid disaggregation of microtubules. The interference with the polymerization/depolymerization cycle in cells appears to interfere with both the replication and migration of cells.

After extensive preclinical screening in mouse tumor models, paclitaxel entered clinical trials in 1983. Over the past few years, paclitaxel has demonstrated good response rates in treating both ovarian and breast cancer patients who were not benefitting from vinca alkaloid or cisplatin therapy. It has also shown encouraging results in patients with other types of cancer including lung, melanoma, lymphoma, head and neck.

For further information, reference may be made to the U.S. National Cancer Institute's Clinical Brochure for Paclitaxel, revised July 1991, and papers presented at the Second National Cancer Institute Workshop on Paclitaxel and Taxus held in Alexandria, Va. USA on Sep. 23–24, 1992.

BRIEF DESCRIPTION OF THE INVENTION

It is a disadvantage of the known formulation that the paclitaxel therein degrades, with the result that the shelf life of the formulation is unsatisfactory, and there is therefore a need for a taxol solution of improved stability.

Accordingly, in a general aspect the invention provides a solution containing paclitaxel, cremophor EL™ and ethanol, characterized in that the pH of the solution has been adjusted into the range 1 to 8 by addition of an acid.

Acids in the form of powders, for example citric acid, are preferred over those which contain water, for example sulfuric acid. The most preferred acid for use in accordance with the present invention is citric acid, but a wide range of acids may be used including the following:

Citric acid—monohydrous
Citric acid—anhydrous
Citric acid—hydrous
Acetic acid
Formic acid
Ascorbic acid
Aspartic acid
Benzene sulphonic acid
Benzoic acid
Hydrochloric acid
Sulphuric acid
Phosphoric acid
Nitric acid
Tartaric acid
Diatrizoic acid
Glutamic acid
Lactic acid
Maleic acid
Succinic acid

DETAILED DESCRIPTION OF THE ILLUSTRATED EMBODIMENTS

Due to its limited solubility in water, Paclitaxel is usually prepared and administered in a vehicle containing cremophor EL™ (a polyethoxylated castor oil which acts as a solubilizer) and ethanol. A commercially available solution supplied by Bristol-Myers Squibb (BMS) is formulated with these components and has a pH of 9.1.

As indicated above, the invention essentially teaches addition of an acid to a paclitaxel formulation to adjust its pH into the range 1 to 8, preferable 5 to 7.

In a preferred procedure adopted by the applicant, which it will be clearly understood is non-limiting, the following steps were carried out:

Mixing Instructions

Solution 1

Citric acid was dissolved in absolute alcohol, using a ratio of 8 mls of absolute alcohol to 1 gram of citric acid, and the solution was stirred for fifteen (15) minutes.

Solution 2

Cremophor EL was weighed out into the main mixing vessel.

Solution 3

Solution 1 was added to solution 2, and the container used for solution 2 was washed with a minimum quantity of absolute alcohol to ensure complete transfer of the citric acid. Solution 3 was mixed and bubbled with nitrogen for at least 15 minutes. The paclitaxel was weighed out and slurried using absolute alcohol, using a ratio of 8 ml of absolute alcohol to 1 gm of taxol. The slurried paclitaxel was added to solution 3 and the slurrying vessel was washed with a minimum quantity of absolute alcohol. Solution 3 was adjusted to 75% of required volume using absolute alcohol, and thoroughly stirred for at least 45 minutes until completely dissolved. Once completely dissolved, the volume was checked and made up as necessary with absolute alcohol and the final solution stirred for 5 minutes.

EXAMPLE 1

A solution was prepared with the following formulation:

| Formulation: (Sample 1) | |
|---|---|
| Cremophor EL | 0.5 mL |
| Citric Acid (Anhydrous) | 2.0 mg |
| Taxol | 6.0 mg |
| Absolute Alcohol | to 1.0 mL |

The pH of this solution was determined as 6.1.

The stability of this sample was compared with a sample prepared by the formulation stated in the NCI Paclitaxel Clinical brochure (as follows) which had a pH of 9.1. (Sample 2)

| Sample 2 | per mL |
|---|---|
| Taxol | 6 mg |
| Cremophor EL | 0.5 mL |
| Absolute Alcohol | to 1 mL |

The solutions were filled into clear type 1 glass 5 mL vials and sealed with rubber bungs.

The solutions were stored at 40° C. for 7 (seven) days and the stability results are shown in Table 1.

| | Sample 1 | Sample 2 |
|---|---|---|
| pH | 6.2 | 9.0 |
| Potency | 96.6 | 86.7 |
| Major individual impurity | 0.3% | 5.1% |
| Total impurities | 1.0% | 12.2% |

Clearly Sample 1 showed significantly increased stability over Sample 2.

EXAMPLE 2

A solution was prepared with the following formulation:

| Formulation: (Sample 3) | |
|---|---|
| Cremophor EL | 0.5 mL |
| Taxol | 6.0 mg |
| Absolute Ethanol | to 1.0 mL | pH adjusted to 6.6 with 1.0M Acetic Acid.

The solution was filled into clear type I glass 5 mL vials and sealed with rubber bungs.

The solution was stored at 40° C. for 7 days.

The stability results obtained are compared to those seen with Sample 2.

| | Sample 3 | Sample 2 |
|---|---|---|
| pH | 6.7 | 9.0 |
| Potency | 97.5 | 86.7 |
| Major individual impurity | 0.3% | 5.1% |
| Total impurities | 2.3% | 12.2% |

Again the significantly superior stability of the formulation according to the invention (Sample 3) is evident.

It will be clearly understood that the invention in its general aspects is not limited to the specific details referred to hereinabove.

What is claimed is:

1. An article of manufacture comprising a sealable container and a pharmaceutical formulation contained therein, said pharmaceutical formulation comprising paclitaxel and a pharmaceutically-acceptable carrier, wherein said pharmaceutical formulation has a pH of about 7 or less, and wherein said pharmaceutical formulation has been sealed in said container for at least seven days.

2. The article of manufacture of claim 1, wherein said pharmaceutical formulation has a pH between 5 and 7, inclusive.

3. The article of manufacture of claim 1, further comprising ethanol as a constituent thereof.

4. The article of manufacture of claim 3, wherein said pharmaceutical formulation has a pH between 5 and 7 inclusive.

5. The article of manufacture of claim 1, wherein said pharmaceutically-acceptable carrier is polyethoxylated castor oil.

6. The article of manufacture of claim 1, wherein said pharmaceutical formulation is anhydrous.

7. The article of manufacture of claim 1, wherein said pharmaceutical formulation comprises an acidifying agent.

8. The article of manufacture of claim 7, wherein said acidifying agent is a mineral acid.

9. The article of manufacture of claim 7, wherein said acidifying agent is an organic acid.

10. The article of manufacture of claim 7, wherein said acidifying agent is acetic acid.

11. The article of manufacture of claim 7, wherein said acidifying agent is citric acid.

12. The article of manufacture of claim 11, wherein said citric acid is anhydrous.

13. A composition of matter produced by the process of:
   (a) obtaining a sealable container;
   (b) obtaining a pharmaceutical formulation comprising paclitaxel and a pharmaceutically-acceptable carrier, wherein said pharmaceutical formulation has a pH of about 7 or less;
   (c) placing said pharmaceutical formulation in said sealable container;
   (d) sealing said sealable container; and
   (e) storing said pharmaceutical formulation in said sealed container for at least seven days.

14. The composition of matter of claim 13, wherein said pharmaceutical formulation has a pH between 5 and 7, inclusive.

15. The composition of matter of claim 13, further comprising ethanol as a constituent thereof.

16. The composition of matter of claim 15, wherein said pharmaceutical formulation has a pH between 5 and 7 inclusive.

17. The composition of matter of claim 13, wherein said pharmaceutically-acceptable carrier is polyethoxylated castor oil.

18. The composition of matter of claim 13, wherein said pharmaceutical formulation is anhydrous.

19. The composition of matter of claim 13, wherein said pharmaceutical formulation comprises an acidifying agent.

20. The composition of matter of claim 19, wherein said acidifying agent is a mineral acid.

21. The composition of matter of claim 19, wherein said acidifying agent is an organic acid.

22. The composition of matter of claim 19, wherein said acidifying agent is acetic acid.

23. The composition of matter of claim 19, herein said acidifying agent is citric acid.

24. The composition of matter of claim 23, wherein said citric acid is anhydrous.

25. An article of manufacture comprising a sealable container and a pharmaceutical formulation contained therein, said pharmaceutical formulation comprising paclitaxel; a pharmaceutically-acceptable carrier; and an acid in sufficient amount to improve the stability of the paclitaxel such that at least 95% of the paclitaxel potency is retained when the composition is stored at 40° C. for seven days; and wherein said pharmaceutical formulation has been sealed in said container for at least seven days.

26. The article of manufacture of claim 25, wherein said pharmaceutical formulation has a pH between 5 and 7, inclusive.

27. The article of manufacture of claim 25, further comprising ethanol as a constituent thereof.

28. The article of manufacture of claim 27, wherein said pharmaceutical formulation has a pH between 5 and 7 inclusive.

29. The article of manufacture of claim 25, wherein said pharmaceutically-acceptable carrier is polyethoxylated castor oil.

30. The article of manufacture of claim 25, wherein said pharmaceutical formulation is anhydrous.

31. The article of manufacture of claim 29, wherein said acid is a mineral acid.

32. The article of manufacture of claim 29, wherein said acid is an organic acid.

33. The article of manufacture of claim 29, wherein said acid is acetic acid.

34. The article of manufacture of claim 29, wherein said acid is citric acid.

35. The article of manufacture of claim 34, wherein said citric acid is anhydrous.

36. A composition of matter produced by the process of:
(a) obtaining a sealable container;
(b) obtaining a pharmaceutical formulation comprising paclitaxel, a pharmaceutically-acceptable carrier, and an acid in sufficient amount to improve the stability of the paclitaxel such that at least 95% of the paclitaxel potency is retained when the composition is stored at 40° C. for seven days;
(c) placing said pharmaceutical formulation in said sealable container;
(d) sealing said sealable container; and
(e) storing said pharmaceutical formulation in said sealed container for at least seven days.

37. The composition of matter of claim 36, wherein said pharmaceutical formulation has a pH between 5 and 7, inclusive.

38. The composition of matter of claim 36, further comprising ethanol as a constituent thereof.

39. The composition of matter of claim 38, wherein said pharmaceutical formulation has a pH between 5 and 7 inclusive.

40. The composition of matter of claim 36, wherein said pharmaceutically-acceptable carrier is polyethoxylated castor oil.

41. The composition of matter of claim 36, wherein said pharmaceutical formulation is anhydrous.

42. The composition of mater of claim 40, wherein said acid is a mineral acid.

43. The composition of matter of claim 40, wherein said acid is an organic acid.

44. The composition of matter of claim 40, wherein said acid is acetic acid.

45. The composition of matter of claim 40, herein said acid is citric acid.

46. The composition of matter of claim 45, wherein said citric acid is anhydrous.

* * * * *

UNITED STATES PATENT AND TRADEMARK OFFICE
CERTIFICATE OF CORRECTION

PATENT NO. : 6,140,359
DATED : October 31, 2000
INVENTOR(S) : David Carver, et al It is certified that error appears in the above-identified patent and that said Letters Patent is hereby corrected as shown below:

Abstract Line 9:
"taxol" should read --paclitaxel--.

Column 1:
Line 10: "taxol" should read --paclitaxel--;
Line 15: "Taxol" should read --paclitaxel;
Line 19: "taxol (paclitaxel)" should read --paclitaxel--;
Line 53: "taxol" should read --paclitaxel--.

Column 2:
Line 60: "taxol" should read --paclitaxel--.

Column 3:
Line 10: "taxol: should read --paclitaxel--;
Line 24: "Taxol" should read --Paclitaxel--;
Line 56: "Taxol" should read --Paclitaxel--.

Column 5:
Line 25: "scaled" should read --sealed--.

Signed and Sealed this

Twelfth Day of June, 2001

*Attest:*

NICHOLAS P. GODICI
*Attesting Officer*   Acting Director of the United States Patent and Trademark Office

UNITED STATES PATENT AND TRADEMARK OFFICE
CERTIFICATE OF CORRECTION

PATENT NO. : 6,140,359
DATED : October 31, 2000
INVENTOR(S) : David Carver, et al It is certified that error appears in the above-identified patent and that said Letters Patent is hereby corrected as shown below:

Abstract Line 9:
"taxol" should read --paclitaxel--.

Column 1:
Line 10: "taxol" should read --paclitaxel--;
Line 15: "Taxol" should read --paclitaxel;
Line 19: "taxol (paclitaxel)" should read --paclitaxel--;
Line 53: "taxol" should read --paclitaxel--.

Column 2:
Line 60: "taxol" should read --paclitaxel--.

Column 3:
Line 10: "taxol: should read --paclitaxel--;
Line 24: "Taxol" should read --Paclitaxel--;
Line 56: "Taxol" should read --Paclitaxel--.

Column 5:
Line 25: "scaled" should read --sealed--.

Signed and Sealed this

Twenty-sixth Day of June, 2001

*Attest:*

NICHOLAS P. GODICI
*Attesting Officer*   Acting Director of the United States Patent and Trademark Office